(12) United States Patent
Zhang et al.

(10) Patent No.: US 8,862,581 B2
(45) Date of Patent: *Oct. 14, 2014

(54) METHOD AND SYSTEM FOR CONCENTRATION DETECTION

(75) Inventors: Haihong Zhang, Singapore (SG); Cuntai Guan, Singapore (SG); Brahim Ahmed Salah Hamadi Charef, Singapore (SG); Chuanchu Wang, Singapore (SG); Kok Soon Phua, Singapore (SG)

(73) Assignee: Agency for Science Technology and Research, Connexis (SG)

( * ) Notice: Subject to any disclaimer, the term of this patent is extended or adjusted under 35 U.S.C. 154(b) by 655 days.

This patent is subject to a terminal disclaimer.

(21) Appl. No.: 12/990,156

(22) PCT Filed: Apr. 28, 2008

(86) PCT No.: PCT/SG2008/000141
§ 371 (c)(1),
(2), (4) Date: Mar. 22, 2011

(87) PCT Pub. No.: WO2009/134205
PCT Pub. Date: Nov. 5, 2009

(65) Prior Publication Data
US 2011/0191350 A1 Aug. 4, 2011

(51) Int. Cl.
*G06F 7/00* (2006.01)
*G06F 17/30* (2006.01)
*A61B 5/16* (2006.01)
*A61B 5/00* (2006.01)
*G06K 9/00* (2006.01)
*A61B 5/048* (2006.01)

(52) U.S. Cl.
CPC .................. *A61B 5/048* (2013.01); *A61B 5/168* (2013.01); *A61B 5/165* (2013.01); *A61B 5/7267* (2013.01); *G06K 9/00523* (2013.01)
USPC ............................ 707/735; 707/750; 707/758

(58) Field of Classification Search
USPC .......................... 707/735, 743, 746, 750, 758
See application file for complete search history.

(56) References Cited

U.S. PATENT DOCUMENTS 5,434,412 A * 7/1995 Sodickson et al. ............ 250/343
5,460,184 A 10/1995 Sato et al.
(Continued)

FOREIGN PATENT DOCUMENTS

WO WO 02/091119 A2 11/2002

OTHER PUBLICATIONS

Besserve et al., "Classification methods for ongoing EEG and MEG signals", Biol Res 40: 2007, pp. 415-437, hereinafter.*

(Continued)

*Primary Examiner* — Daniel Kuddus
(74) *Attorney, Agent, or Firm* — Christensen Fonder P.A.

(57) ABSTRACT

There is a method and a system for concentration detection. The method for concentration detection includes the steps of extracting temporal features from brain signals; classifying the extracted temporal features using a classifier to give a score $x_1$; extracting spectral-spatial features from brain signals; selecting spectral-spatial features containing discriminative information between concentration and non-concentration states from the set of extracted spectral-spatial features; classifying the selected spectral-spatial features using a classifier to give a score $x_2$; combining the scores $x_1$ and $x_2$ to give a single score; and determining if the subject is in a concentration state based on the single score.

19 Claims, 16 Drawing Sheets

(56) References Cited

U.S. PATENT DOCUMENTS

| | | | |
|---|---|---|---|
| 5,724,987 A * | 3/1998 | Gevins et al. | 600/544 |
| 5,915,250 A * | 6/1999 | Jain et al. | 1/1 |
| 5,983,129 A | 11/1999 | Cowan et al. | |
| 5,991,032 A * | 11/1999 | Atkinson et al. | 356/437 |
| 6,061,141 A * | 5/2000 | Goldenberg et al. | 356/437 |
| 6,067,467 A * | 5/2000 | John | 600/544 |
| 6,075,252 A * | 6/2000 | Atkinson et al. | 250/559.4 |
| 6,097,980 A * | 8/2000 | Monastra et al. | 600/544 |
| 6,137,104 A * | 10/2000 | Webb et al. | 250/226 |
| 6,287,765 B1 * | 9/2001 | Cubicciotti | 435/6.11 |
| 6,355,386 B1 * | 3/2002 | Helber et al. | 430/20 |
| 6,420,709 B1 * | 7/2002 | Block et al. | 250/343 |
| 6,468,709 B2 * | 10/2002 | Aylward et al. | 430/207 |
| 6,520,921 B1 | 2/2003 | Patton et al. | |
| 6,930,773 B2 * | 8/2005 | Cronin et al. | 356/300 |
| 7,054,810 B2 * | 5/2006 | Gao et al. | 704/231 |
| 2002/0099295 A1 * | 7/2002 | Gil et al. | 600/476 |
| 2003/0228565 A1 * | 12/2003 | Oestreicher et al. | 435/4 |
| 2003/0228585 A1 * | 12/2003 | Inoko et al. | 435/6 |
| 2004/0152995 A1 | 8/2004 | Cox et al. | |

OTHER PUBLICATIONS

Spurbeck et al.. "Least Squares Approximation of Perfect Reconstruction Filter Banks". IEEE Transactions on Signal Processing. vol. 46, No. 4, Apr. 1998, pp. 968-978.*

Ang et al.. "Filter Bank Common Spatial Pattern (FBCSP) in Brain-Computer Interface". IEEE, 2008, pp. 2390-2397.*

Zhou et al., "Classifying mental tasks based on features of higher-order statistics from EEG signals in brain-computer interface", Elsevier Inc. 2007.*

Bostanov BCCI Competition 2003—Data Sets Ib and IIb: Feature Extraction From Event-Related Brain Potentials with the Continuous Wavelet Transform and the t-value Scalogram, IEEE Transactions on Biomedical Engineering, Jun. 2004, vol. 51(6), pp. 1057-1061.*

Besserve et al., Classification methods for ongoing EEG and MEG signals, Published by: Biological Research. Year: 2007.*

Molteni, Erika, et al., "Analysis of the dynamical behavior of the EEG rhythms during a test of sustained attention," *Proceedings of the 20th Annual International Conference of the IEEE Engineering in Medicine and Biology Society (EMBS)*, Aug. 22-26, 2007, pp. 1298-1301.

Monastra, Vincent J., et al., "Electroencephalographic Biofeedback in the Treatment of Attention-Deficit/Hyperactivity Disorder," *Applied Psychophysiology and Biofeedback*, vol. 30, No. 2, Jun. 2005, pp. 95-114.

Jung, Tzyy-Ping, et al., "Estimating Alertness from the EEG Power Spectrum," *IEEE Transactions on Biomedical Engineering*, vol. 44, No. 1, Jan. 1997, pp. 60-69.

Ang, Kai Keng, et al., "Filter Bank Common Spatial Pattern (FBCSP) in Brain-Computer Interface," *Proceedings of World Congress Computational Intelligence*, 2008, pp. 2390-2397.

Haufler, Amy J., et al., "Neuro-cognitive activity during a self-paced visuospatial task: comparative EEG profiles in marksmen and novice shooters," *Biological Psychology*, vol. 53, No. 2-3, Jul. 2000, pp. 131-160.

Mann, Christopher A., "Quantitative Analysis of EEG in Boys with Attention-deficit-hyperactivity Disorder: Controlled Study with Clinical Implications," *Pediatric Neurology*, vol. 8, No. 1, Jan.-Feb. 1992, pp. 30-36.

Monastra, Vincent J., "The Effects of Stimulant Therapy, EEG Biofeedback, and Parenting Style on the Primary Symptoms of Attention-Deficit/Hyperactivity Disorder," *Applied Psychophysiology and Biofeedback*, vol. 27, No. 4, Dec. 2002, pp. 231-249.

Bostanov, Vladimir, "BCI Competition 2003—Data Sets Ib and IIb: Feature Extractions From Event-Related Brain Potentials With the Continuous Wavelet Transform and the t-Value Scalogram," *IEEE Transactions on Biomedical Engineering*, vol. 51, No. 6, Jun. 2004, pp. 1057-1061.

Wei, Jinhe, et al., "The temporal and spatial features of event-related EEG spectral changes in 4 mental conditions," *Electroencephalography and clinical neurophysiology*, vol. 106, 1998, pp. 416-423.

* cited by examiner

METHOD AND SYSTEM FOR CONCENTRATION DETECTION

PRIORITY CLAIM

The present application is a National Phase entry of PCT Application No. PCT/SG2008/000141, filed Apr. 28, 2008, the disclosure of which is hereby incorporated by reference herein in its entirety.

FIELD OF INVENTION

The present invention relates broadly to a method and system for concentration detection.

BACKGROUND

Concentration detection methods can be used in various applications such as in the diagnosis of neuro-cognitive conditions, for example, the Attention Deficit or Hyperactivity Disorder (ADHD). In addition, they can be used for performance monitoring and enhancement in sports, gaming, driving etc. or for assessing work related stress. Concentration detection methods can also be used to monitor the effectiveness of medication such as in clinical drug trials or the effectiveness of therapy and rehabilitation such as biofeedback.

In general, it is preferable that a concentration detection method allows a continuous detection and measurement of the concentration or attention levels. Furthermore, a concentration detection method needs to be accurate and robust. It is also preferable for the concentration detection method to be easily used and to be of a low cost.

Monastra and Lubar [Monastra and Lubar, 2000—U.S. Pat. No. 6,097,980—Quantitative electroencephalographic (QEEG) process and apparatus for assessing attention deficit hyperactivity disorder; V. J. Monastra, S. Lynn, M. Linden, J. F. Lubar, J. Gruzelier, and T. J. LaVaque, "Electroencephalographic Biofeedback in the Treatment of Attention-Deficit/Hyperactivity Disorder," Applied Psychophysiology and Biofeedback, vol. 30, no. 2, pp. 95-114, June 2005.] described a method to calculate an attention index for concentration detection. This attention index is calculated as the average of the theta over beta power ratio for each of the following tasks to be performed by the subject. In these tasks, the subject has to keep his or her eyes open with a fixed gaze (used as the baseline), read, listen or draw. The calculation of the attention index is shown in Equation (1) whereby $EEGpower_{theta}^{Task}$ is the theta power, $EEGpower_{beta}^{Task}$ is the beta power and N is the total number of tasks performed. The theta band is defined as 4-8 Hz whereas the beta band is defined as 13-21 Hz.

$$\text{Attention Index} = \frac{1}{N} \sum_{Task=1}^{N} \frac{EEGpower_{theta}^{Task}}{EEGpower_{beta}^{Task}} \quad (1)$$

FIG. 1 shows graphs illustrating the basis for development of another prior art Cox et al [Cox et al, 2004—US20040152995A1—Method, apparatus, and computer program product for assessment of attentional impairments]. FIGS. 1A and 1B are graphical representations of the EEG frequency dimension, illustrating the EEG power spectrum for two cognitive tasks for a consistent EEG transition case and an inconsistent EEG transition case respectively. In each of the FIGS. 1A and 1B, curves 102A and 102B represent the power spectrum of a subject performing a task and curves 104A and 104B represent the power spectrum of the same subject while performing an adjacent task. In FIG. 1A, curve 102A is above curve 104A at lower frequencies and mostly below curve 104A at higher frequencies (above 16 Hz). This shows that a shift from one task to another (from curve 102A to 104A) results in an increase of higher frequencies and a decrease of lower frequencies. In contrast, in FIG. 1B, no specific change in the frequency distribution over the two tasks is observed.

The EEG consistency shown in FIG. 1 is used as a basis for development of Cox et al. With this basis, Cox et al described two measures for the assessment of attentional impairments. The first measure is the Consistency index (CI) calculated as the EEG power change distance (PCD) transition from one task to another as shown in Equation (2). In Equation (2), N represents the total number of tasks and $\delta_i$ represents whether the PCD is above ($\delta_i=1$), equal to ($\delta_i=0$) or below ($\delta_i=-1$) a cutoff value.

$$\sum_{belowcutoff} \delta_i$$

represents the sum of $\delta_i$ below the cutoff value and $$\sum_{abovecutoff} \delta_i$$

represents the sum of $\delta_i$ above the cutoff value.

$$CI = 100 \left| \frac{1}{N} \left( \sum_{belowcutoff} \delta_i - \sum_{abovecutoff} \delta_i \right) \right| \quad (2)$$

The second measure in Cox et al is the Alpha Blockade Index (ABI) which is based on the spectral analysis, particularly of the alpha activity in the brain. The calculation of the ABI is given in Equation (3). In Equation 3, $\alpha_i$ represents the alpha power in the subject's brain during the $i^{th}$ task or the $i^{th}$ resting period and k represents the total number of tasks and resting periods.

$$ABI = \frac{100}{k-1} \sum_{i=2}^{k} \left| \frac{\alpha_i - \alpha_{i-1}}{\max(\alpha_{i-1}, \alpha_i)} \right| \quad (3)$$

Cowan and Prell [Cowan and Prell, 1999—U.S. Pat. No. 5,983,129—Method for determining an individual's intensity of focused attention and integrating same into computer program] proposed to use EEGs collected from the frontal lobe of the subject's brains and defined an Attention Indicator that is inversely proportional to a mathematical transformation of an amplitude measure of the frontal lobe EEG. The frontal lobe EEG is within the frequency band of 0-11 Hz. However, since the amplitude of the EEG changes over time and varies significantly across different subjects, the method in Cowan and Prell is unable to provide a quantifiable level of attention.

Other prior arts for implementing concentration detection methods are as follows: E. Molteni, A. M. Bianchi, M. Butti, G. Reni, C. Zucca, "Analysis of the dynamical behaviour of the EEG rhythms during a test of sustained attention" Proceeding of the 29th Annual International Conference of the IEEE Engineering in Medicine and Biology Society, 2007. EMBS 2007), Aug. 22-26, 2007, pp. 1298-1301; C. A. Mann, J. F. Lubar, A. W. Zimmerman, C. A. Miller, and R. A. Muenchen, "Quantitative analysis of EEG in boys with attention deficit-hyperactivity disorder: Controlled study with clinical implications," Pediatric Neurology, vol. 8, no. 1, pp. 30-36, January-February 1992.; A. J. Haufler, T. W. Spalding, D. L. Santa Maria, and B. D. Hatfield, "Neuro-cognitive activity during a self-paced visuospatial task: comparative EEG profiles in marksmen and novice shooters," Biological Psychology, vol. 53, no. 2-3, pp. 131-160, July 2000.; T.-P. Jung, S. Makeig, M. Stensmo, and T. J. Sejnowski, "Estimating alertness from the EEG power spectrum," IEEE Transactions on Biomedical Engineering, vol. 44, no. 1, pp. 60-69, 1997.

None of the prior art methods can provide quantifiable measures, for example 1-100 marks, for the level of attention detected. In addition, the prior art methods were based on spectral analysis and are hence inherently sensitive to all kinds of variations, for example, variations due to artefacts, noises, measurement devices, etc. The prior art methods are also unable to provide a consistent measure across different subjects.

FIG. 2 shows a flowchart 200 illustrating the general process of concentration detection methods in the prior arts based on spectral analysis. As shown in FIG. 2, in the prior arts, a frequency analysis step 202 is performed on the acquired EEG. Next, an Index is generated in step 204 to give an Attention indicator for concentration detection.

Hence, in view of the above, there exists a need for a method and system for concentration detection which seek to address at least one of the above problems.

SUMMARY

According to a first aspect of the present invention, there is provided a method for concentration detection, the method comprising the steps of extracting temporal features from brain signals; classifying the extracted temporal features using a classifier to give a score $x_1$; extracting spectral-spatial features from brain signals; selecting spectral-spatial features containing discriminative information between concentration and non-concentration states from the set of extracted spectral-spatial features; classifying the selected spectral-spatial features using a classifier to give a score $x_2$; combining the scores $x_1$ and $x_2$ to give a single score and determining if the subject is in a concentration state based on the single score.

The step of extracting temporal features from brain signals may further comprise the steps of computing statistics of brain waveforms in each of a plurality of electrode channels and concatenating the statistics into a joint feature vector.

The statistics of the brain waveforms may be standard deviations.

The step of extracting spectral-spatial features of brain signals may further comprise the steps of extracting respective brain signal components in discrete frequency windows using filter banks to obtain spectral features of brain signals and applying a CSP algorithm to each of the spectral features using a CSP array to obtain the spectral-spatial features of brain signals.

The filter banks may comprise low-order bandpass Chebyshev Type II filters with a pass-band width of 4 Hz.

The step of selecting spectral-spatial features containing discriminative information between concentration and non-concentration states from the set of extracted spectral-spatial features may further comprise the step of selecting spectral-spatial features based on the mutual dependence of the features with respect to the concentration and non-concentration states.

The step of combining the scores $x_1$ and $x_2$ to give a single score may further comprise the steps of normalizing the scores $x_1$ and $x_2$ according to an equation $(x-m_x)/s_x$ whereby $m_x$ and $s_x$ are the mean and standard deviation of outputs from the classifiers using training samples to give $x_{1n}$ and $x_{2n}$ respectively; assigning weights $w_1$ and $w_2$ to normalized scores $x_{1n}$ and $x_{2n}$ respectively; and combining the scores $x_{1n}$ and $x_{2n}$ according to an equation $x_{1n}*w_1+x_{2n}*w_2$ to give a single score.

The weights $w_1$ and $w_2$ may be calculated according to the equation $w_i=(y_i)^p$ where $y_i$ is the classification accuracy in classifying the extracted temporal features if i=1 and in classifying the extracted spectral-spatial features if i=2 and p (p>0) controls the power of $w_i$ in the calculation of the single score.

The step of determining if the subject is in a concentration state based on the single score may further comprise determining that the subject is in a concentration state if the single score is higher than a threshold and that the subject is not in a concentration state if the single score is lower than a threshold.

The classifier may comprise one or more of a group consisting of a Linear Discriminant Analysis classifier, Neural Networks, Support Vector Machines, Fuzzy Inference System, Tree-based classifiers, Fuzzy Type 2 and Relevance Vector Machine.

The method may further comprise the step of using training data to generate parameters for classifying the extracted temporal features using a classifier, for extracting spectral-spatial features from brain signals, for selecting spectral-spatial features containing discriminative information between the concentration and non-concentration states from the set of extracted spectral-spatial features and for classifying the selected spectral-spatial features using a classifier.

The parameters may comprise one or more of a group consisting of projection matrices of CSPs for the CSP algorithm, parameters for selecting spectral-spatial features based on mutual information and a model for the classifiers.

The step of using training data to generate parameters may further comprise the steps of collecting training data from subjects performing a set of tasks and determining said parameters via machine learning methods.

The set of tasks may comprise one or more of a group consisting of reading a technical paper, performing mental arithmetic with closed eyes, relaxing and looking around, and resting with closed eyes.

According to a second aspect of the present invention, there is provided a system for concentration detection, the system comprising a temporal feature extracting unit for extracting temporal features from brain signals; a temporal feature classifying unit for classifying the extracted temporal features using a classifier to give a score $x_1$; a spectral-spatial feature extracting unit for extracting spectral-spatial features from brain signals; a spectral-spatial feature selecting unit for selecting spectral-spatial features containing discriminative information between the concentration and non-concentration states from the set of extracted spectral-spatial features; a spectral-spatial feature classifying unit for classifying the selected spectral-spatial features using a classifier to give a score $x_2$ and a processing unit coupled to said temporal feature classifying unit and said spectral-spatial feature classifying unit for combining the scores $x_1$ and $x_2$ to give a single score and for determining if the subject is in a concentration state based on the single score.

The system may further comprise filter banks to extract respective brain signal components in discrete frequency windows to obtain spectral features of brain signals and a CSP array to apply a CSP algorithm to each of the spectral features to obtain the spectral-spatial features of brain signals;

The filter banks may comprise low-order bandpass Chebyshev Type II filters with a pass-band width of 4 Hz.

According to a third aspect of the present invention, there is provided a data storage medium having stored thereon computer code means for instructing a computer system to execute a method for concentration detection, the method comprising the steps of extracting temporal features from brain signals; classifying the extracted temporal features using a classifier to give a score $x_1$; extracting spectral-spatial features from brain signals; selecting spectral-spatial features containing discriminative information between the concentration and non-concentration states from the set of extracted spectral-spatial features; classifying the selected spectral-spatial features using a classifier to give a score $x_2$; combining the scores $x_1$ and $x_2$ to give a single score and determining if the subject is in a concentration state based on the single score.

According to a fourth aspect of the present invention, there is provided a method for concentration detection, the method comprising the steps of extracting features from brain signals; selecting features containing discriminative information between concentration and non-concentration states from the set of extracted features; classifying the selected features using a classifier to give a score; wherein subject dependant training data is used to generate parameters for extracting the features from the brain signals, for selecting the features containing discriminative information between the concentration and non-concentration states from the set of extracted features and for classifying the selected features using a classifier; and determining if the subject is in a concentration state based on the score.

According to a fifth aspect of the present invention, there is provided a system for concentration detection, the system comprising a feature extracting unit for extracting features from brain signals; a feature selecting unit for selecting features containing discriminative information between concentration and non-concentration states from the set of extracted features; a feature classifying unit for classifying the selected features using a classifier to give a score; wherein subject dependant training data is used to generate parameters for extracting the features from the brain signals, for selecting the features containing discriminative information between the concentration and non-concentration states from the set of extracted features and for classifying the selected features using a classifier; and a processing unit for determining if the subject is in a concentration state based on the score.

According to a sixth aspect of the present invention, there is provided a data storage medium having stored thereon computer code means for instructing a computer system to execute a method for concentration detection, the method comprising the steps of extracting features from brain signals; selecting features containing discriminative information between concentration and non-concentration states from the set of extracted features; classifying the selected features using a classifier to give a score; wherein subject dependant training data is used to generate parameters for extracting the features from the brain signals, for selecting the features containing discriminative information between the concentration and non-concentration states from the set of extracted features and for classifying the selected features using a classifier; and determining if the subject is in a concentration state based on the score.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
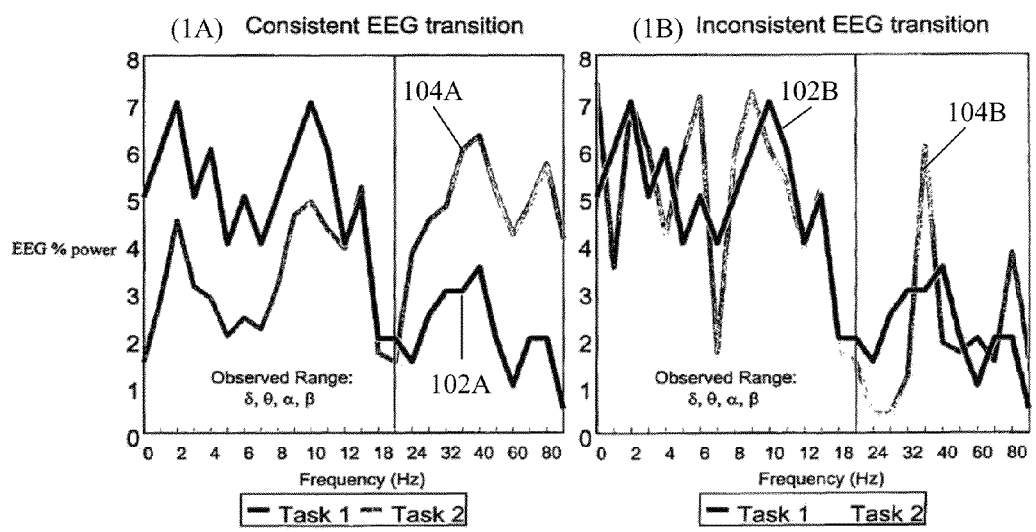
FIGS. 1a and b show graphs illustrating the basis for development of a prior art.
Figure 2:
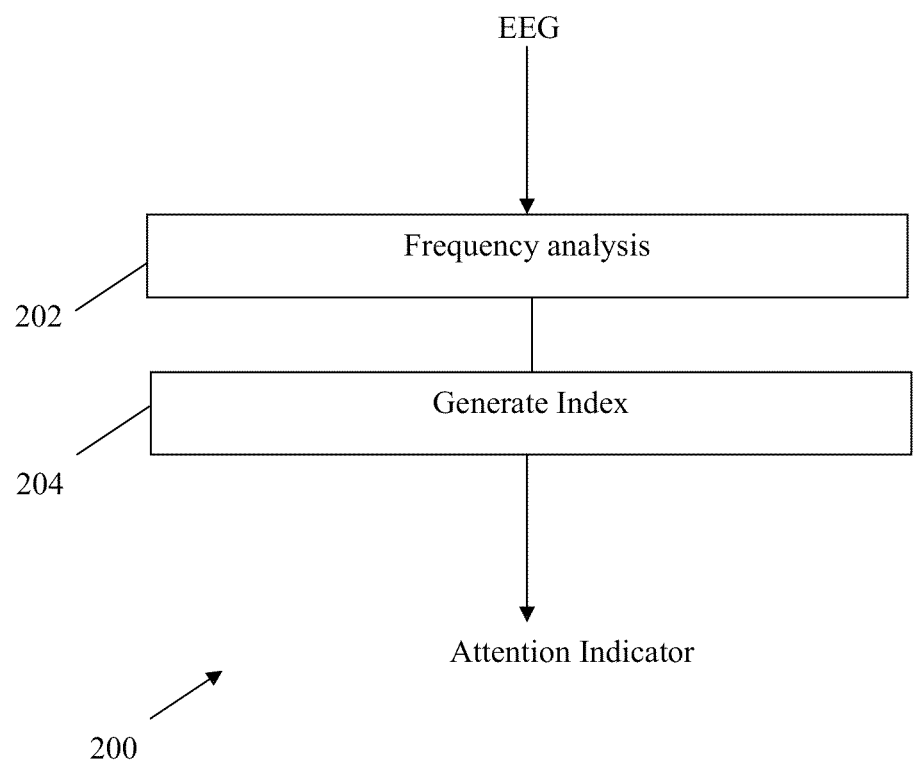
FIG. 2 shows a flowchart illustrating the general process of concentration detection methods in the prior arts.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "calculating", "determining", "generating", "outputting", "extracting", "classifying", "selecting", "combining", "computing", "concatenating", "applying", "normalizing", "assigning" or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses an apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

Embodiments of the present invention seek to overcome the limitations of the prior arts by using a more advanced approach named "Hybrid EEG Model".

Figure 3:
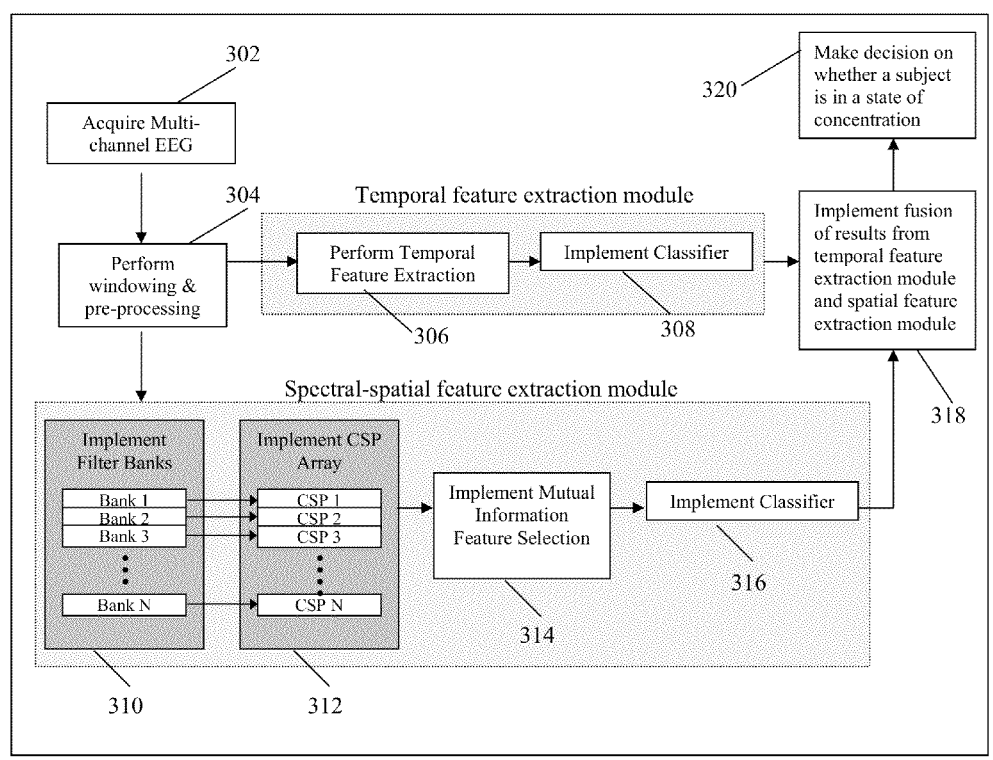
FIG. 3 shows a flowchart illustrating a method for concentration detection according to an embodiment of the present invention.

FIG. 3 shows a flowchart illustrating a method 300 for concentration detection according to an embodiment of the present invention. In step 302, multi-channel EEG acquisition is performed using a real-time data acquisition and processing platform. In one example, the data acquisition and processing platform implements the following steps. A NuAmps device from Neuroscan, Inc. is first used to measure the scalp brain signals. The brain signals are then recorded from Ag—AgCl electrodes placed on the surface of the user's head. The digitizer device for the recording of the brain signals works at a sampling rate of 250 Hz. The recorded brain signals are then filtered via temporal filtering to remove high frequency noises and very slow waves using for example, a $5^{th}$-order digital Butterworth filter with a passband of [0.5 Hz 40 Hz]. The filtered brain signals are next downsampled by a factor of 4 in order to reduce the computational complexity.

In step 304, windowing and pre-processing are performed. Step 304 selects electrode channels of interest and segments the incoming data stream into chunks using a running windowing mechanism. The window size and shift step are determined using training data. Step 304 also removes noise and artefacts through filtering.

In step 306, temporal feature extraction is performed. Step 306 computes statistics such as the standard deviation of the windowed and pre-processed EEG waveforms in each channel. The statistics are then concatenated into a joint feature vector. The feature vector is then input to step 308. In step 308, a classifier, such as the Linear Discriminant Analysis (LDA), is implemented to produce a score, for example $x_1$, indicating the likelihood of the hypothesis whereby the hypothesis is that the subject is in a state of concentration i.e. with focused attention. Other classifiers that can be used include Neural Networks (NNs), Support Vector Machines (SVM), Fuzzy Inference System (FIS), Tree-based classifiers etc., and their variants such as the Fuzzy Type 2 and the Relevance Vector Machine (RVM). Steps 306 and 308 form the temporal feature extraction module in the method 300.

In step 310, an array of band pass filters i.e. filter banks is implemented on the windowed and pre-processed EEG. Each filter bank is centred at a particular frequency, sampled at a fixed interval and is used to extract the EEG component in each discrete frequency window. For example, the fixed interval may be 4 Hz for the frequency range of the EEG from 4 Hz to 36 Hz. In one example, the filter bank is a digital filter with a low order and a linear phase. Such a filter bank can be a Finite Impulse Response (FIR) filter or an Infinite Impulse Response (IIR) filter. In a preferred embodiment, the filter bank is a low-order bandpass Chebyshev Type II filter with a pass-band width of 4 Hz. MATLAB (MathWorks Inc.) tools can be used to design and implement the filter banks. At the output of the filter banks, an EEG component is obtained for each filter bank with each component further containing separate components from each of the selected electrode channels.

In step 312, a common spatial pattern (CSP) array is implemented. Step 312 applies the CSP algorithm to each EEG component obtained in step 310 to emphasize the difference in spatial distributions of the energy between the two classes, the concentration and the non-concentration classes corresponding to the brain states during which the subject is concentrating and not concentrating respectively. The CSP algorithm is detailed in Equation (4) whereby for the $j^{th}$ EEG component, a CSP feature cf(j) is extracted according to Equation (4). In Equation (4), $W_j$ is a matrix comprising of the first $I_1$ and the last $I_2$ rows of W, whereby $I_1$ and $I_2$ are normalized for data processing efficiency and the ratio between $I_1$ and $I_2$ is kept constant. Furthermore, $E_j$ is a m×n data matrix of the $j^{th}$ EEG component whereby m is the number of selected electrode channels and n is the number of samples in the EEG component in one channel. The relationship between W and the covariance matrices of the EEG components is given by Equation (5) in which $\Sigma^{(1)}$ and $\Sigma^{(2)}$ are the covariance matrices of the EEG components corresponding to two different classes of brain signals (i.e. different brain states), I is the identity matrix and D is a diagonal matrix.

$$cf(j) = \text{diag}\left(W_l \frac{E_j E_j^T}{\text{trace}(E_j E_j^T)} W_l^T\right) \quad (4)$$

$$W\Sigma^{(1)}W^T = D, \; W\Sigma^{(2)}W^T = I - D \quad (5)$$

The spatial filtering parameters i.e. spatial patterns such as the matrix W are learnt from the examples of the two classes via a subject dependent model training approach which would be elaborated later. The CSP array produces an array of spectral-spatial features, each representing the energy of the EEG component projected onto a particular spatial pattern. Such an array of features is usually over-redundant since not every spectral-spatial feature is associated with the concentration or non-concentration state in the brain. Preferably, the unnecessary (i.e. redundant) features are removed.

In step 314, a mutual information feature selection is implemented to remove the unnecessary features. Step 314 selects a set of features that contains the discriminative information between the concentration and the non-concentration states. This set is determined through a model training procedure via a subject dependent model training approach which would be elaborated later. At the end of step 314, a feature vector is obtained and is input into step 316.

In step 316, a classifier such as the LDA is implemented. Using the feature vector input from step 314, a score, for example $x_2$, is produced by the classifier. This score indicates the likelihood of the hypothesis whereby the hypothesis is that the subject is in a state of concentration i.e. with focused attention. Steps 310-316 form the spectral-spatial feature extraction module of the method 300.

Step 318 implements the fusion of the results from the temporal feature extraction module and the spectral-spatial feature extraction module to obtain a single output. In step 318, the continuous outputs of the classifiers in the temporal feature extraction module and the spectral-spatial feature extraction module are normalized. In one example, if an output is the score x, the normalized output $x_n$ will be $(x-m_x)/s_x$ whereby $m_x$ and $s_x$ are respectively the mean and standard deviation of the outputs obtained using the training samples Two normalized outputs $x_1$ and $x_{2n}$ from the temporal feature module and the spectral-spatial module respectively are hence obtained. In one example, these two normalized outputs $x_{1n}$ and $x_{2n}$ are combined according to Equation (6) using weights $w_1$ and $w_2$ whereby weights $w_1$ and $w_2$ correspond to $x_{1n}$ and $x_{2n}$ respectively and reflect the individual performance of each of the modules. However, the normalized outputs $x_{1n}$ and $x_{2n}$ can also be combined using non-linear methods such as a non-linear weighted regression. Weights $w_1$ and $w_2$ are calculated according to the formula $w_i = (y_i)^p$ where $y_i$ is the classification accuracy of the module alone and is obtained via training samples, and p (p>0) controls the power of the accuracy's weight in the combination. In one example, p is set to 1.

$$\text{Output} = x_{1n} * w_1 + x_{2n} * w_2 \quad (6)$$

In step 320, a decision on whether the subject is in a state of concentration is made by comparing the combined output obtained in step 318 against a threshold. If the combined output is larger than the threshold, it is decided that the subject is in a state of concentration. Otherwise, it is decided that the subject is not in a state of concentration. The threshold is determined using training samples based on the desired trade-off between the false positive rate and the true positive rate, both of which are important indicators of the performance of a concentration detection method.

Because of the large cross-subject variances in EEG patterns, a subject-dependent model training approach is used in the embodiments of the present invention to obtain the parameters and models for the method 300.

Figure 4:
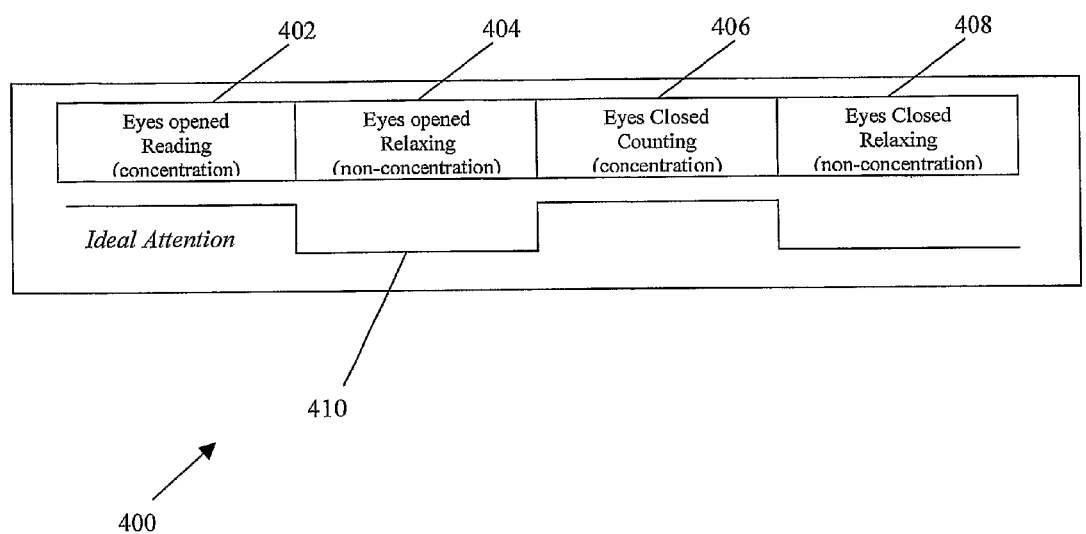
FIG. 4 illustrates a data collection protocol for a subject-dependent model training approach according to an embodiment of the present invention.

In the subject-dependent model training approach in the example embodiments, training data collection sessions are implemented to collect a subject's EEGs during navigated sessions. FIG. 4 illustrates a data collection protocol 400 for the subject-dependent model training approach according to an embodiment of the present invention. The protocol consists of 4 different tasks to be performed by the subject. In task 402, a subject is required to read a technical paper hence, in this task, the subject is in a state of concentration with his or her eyes opened. In task 404, the subject is required to perform mental arithmetic for example, taking 400 minus 7 repeatedly, hence, in this task, the subject is in a state of concentration with his or her eyes closed. In task 406, the subject is required to relax and look around hence, in this task, the subject is not in a state of concentration and has his or her eyes opened. In task 408, the subject is required to have his or her body and mind in a resting state with his or her eyes closed, hence in this task, the subject is not in a state of concentration with his or her eyes closed. The ideal level of attention for each of these tasks is plotted in FIG. 4 as line 410 whereby the ideal level of attention is high when the subject is required to be in a state of concentration and is low when the subject is required to be not in a state of concentration. In one example, the subject is required to take part in a few sessions, each session involving an array of alternate tasks.

Furthermore, in the subject-dependent training approach in the example embodiments, groups of parameters are determined via machine learning methods An example of a machine learning method is the automation parameter optimization which is an iterative approach. Further details of the machine learning methods are given below. In one example, three groups of parameters are generated.

Firstly, projection matrices of CSPs for the CSP algorithm in the spectral-spatial feature extraction module (See FIG. 3) are obtained. The learning of these projection matrices are carried out using the CSP method that jointly diagonalizes the two covariance matrices of the two classes i.e. the concentration class and the non-concentration class.

In one example, the CSP method includes the following steps.

In step 1, the normalized spatial covariance $\Sigma$ of the EEG measurements is computed according to Equation (7). In Equation (7), E is an N×T matrix representing the raw EEG measurement data of a single trial, N is the number of channels, T is the number of measurement samples per channel, ' denotes the transpose operator and trace(·) denotes the operation that sums the diagonal elements.

$$\Sigma = \frac{EE'}{\text{trace}(EE')} \quad (7)$$

In step 2, the composite spatial covariance $\Sigma_c$ is computed according to Equation (8). In Equation (8), the spatial covariance of one distribution $\Sigma_d$ is taken to be the average over the trials of each class and $d \in \{1, 2\}$ is the class index.

$$\Sigma_c = \Sigma_1 + \Sigma_2 \quad (8)$$

In step 3, the whitening transformation matrix P is computed according to Equation (9). In Equation (9), I is the identity matrix.

$$P\Sigma_c P' = I \quad (9)$$

In step 4, the whitened spatial covariance of the two classes is computed according to Equation (10). In Equation (10), $\Sigma_1$ and $\Sigma_2$ share common eigenvectors B as shown in Equation (11) where I is the identity matrix and $\lambda$ is the diagonal matrix of eigenvalues.

$$\Sigma_1 = P\overline{\Sigma}_1 P' \text{ and } \Sigma_2 = P\overline{\Sigma}_2 P' \quad (10)$$

$$\Sigma_1 = B\lambda B' \text{ and } \Sigma_2 = B(I-\lambda)B' \quad (11)$$

In step 5, the CSP projection matrix W is computed according to Equation (12). In Equation (12), the rows of W are the stationary spatial filters and the columns of $W^{-1}$ are the common spatial patterns.

$$W = B'P \quad (12)$$

The spatial filtered signal Z of a single trial EEG E is given according to Equation (13).

$$Z = WE \quad (13)$$

The spatial filtered signal Z given in Equation (13) maximizes the difference in the variance of the two classes of EEG measurements. In general, the variances of only a small number m of the spatial filtered signals are used as features for classification. The signals $Z_p$, $p \in \{1 \ldots 2m\}$ that maximize the difference in the variance of the two classes of EEG are associated with the largest eigenvalues $\lambda$ and $(I-\lambda)$. In one example, these signals are used to form the feature vector $X_p$ given in Equation (14) whereby feature vectors $X_p$ are inputs to the classifier.

$$X_p = \log\left(\text{var}(Z_p) \Big/ \sum_{i=1}^{2m} \text{var}(Z_p)\right) \quad (14)$$

Secondly, a set of parameters for mutual information feature selection in the spectral-spatial feature selection module is determined. The mutual information feature selection method is based on mutual information which indicates the mutual dependence of the features with respect to the classes. Further details of the mutual information feature selection process are as follows.

Taking into consideration a vector variable X for example, CSP features as obtained in Equation (14) and its corresponding class label Y, the mutual information between the two random variables X and Y is given by Equation (15). In Equation (15), H(X) denotes the entropy of the feature variable X and H(Y|X) represents the conditional entropy of class label variable Y given feature variable X. The entropy and the conditional entropy are given respectively in Equation (16) and Equation (17).

$$I(X;Y) = H(X) - H(Y|X) \quad (15)$$

$$H(X) = -\int_{x \in X} xp(x)\log_2 p(x)\,dx \quad (16)$$

$$H(Y|X) = -\int_{x \in X} p(x) \sum_{y \in Y} P(y|x)\log_2 p(y|x)\,dx \quad (17)$$

In one example, the mutual information feature selection process includes the following steps.

In step 1, a candidate set of d features is initialized as $F=\{f_1, f_2, \ldots, f_d\}$ and a select feature set is initialized as a null set Fopt=ø.

In step 2, for each feature $f_k$ in the candidate set, a tentative feature vector $F_k = \text{Fopt} \cup \{fk\}$ is formed. Next, $F_k$ and the Naïve Bayesian Parzen Window are used to predict the class label $Y_k$. The mutual information of the predicted class label and the true label i.e. $I(Y_k; Y)$ is then computed.

In step 3, the feature $f_k$ which maximizes $I(Y_k; Y)$ is then selected.

In step 4, if F=ø and the gain in the mutual information is less than a preset threshold $\delta$ i.e. $I(Y_k;Y)-I_0<\delta$, the process is terminated. Otherwise, in step 5, $I_0=I(Y_k;Y)$.

In step 6, the candidate set is updated by $F \rightarrow F \setminus \{f_k\}$ whereas the select feature set is updated by $\text{Fopt} \rightarrow \text{Fopt} \cup S\{f_k\}$.

In step 7, if the candidate set is empty, the process is terminated. Otherwise, the process is repeated from step 2.

In the example embodiments, a feature refers to a CSP feature from a filter bank and can take on different values at different instances. The mutual information feature selection process in the example embodiments as described above is applied to the training set with labelled samples. After the feature selection process is completed, the select set of features includes the CSP features determined as "important" or characteristic for concentration detection based on their mutuality amongst the labeled samples. This set of features is used during the feature selection process when processing unlabelled data for concentration detection.

Thirdly, models for the classifiers in the method 300 are obtained by the traditional Fisher linear discriminant method, using labelled training data samples. In one example, the labelled training data samples have positive labels if they are recorded from the concentration tasks and negative labels if they are recorded from the non-concentration tasks.

In the example embodiments, the set of parameters obtained from the subject dependent training approach can be used to recreate a model for concentration detection using a computer program. In one example, a setup/configuration file is created whereby this file includes the projection vector and the bias of the classifiers, projection matrices of each CSP filter, the bands to be selected for the filter banks, and the weights to be used for combining the outputs from the temporal feature extraction module and the spectral-spatial feature extraction module.

Figure 5:
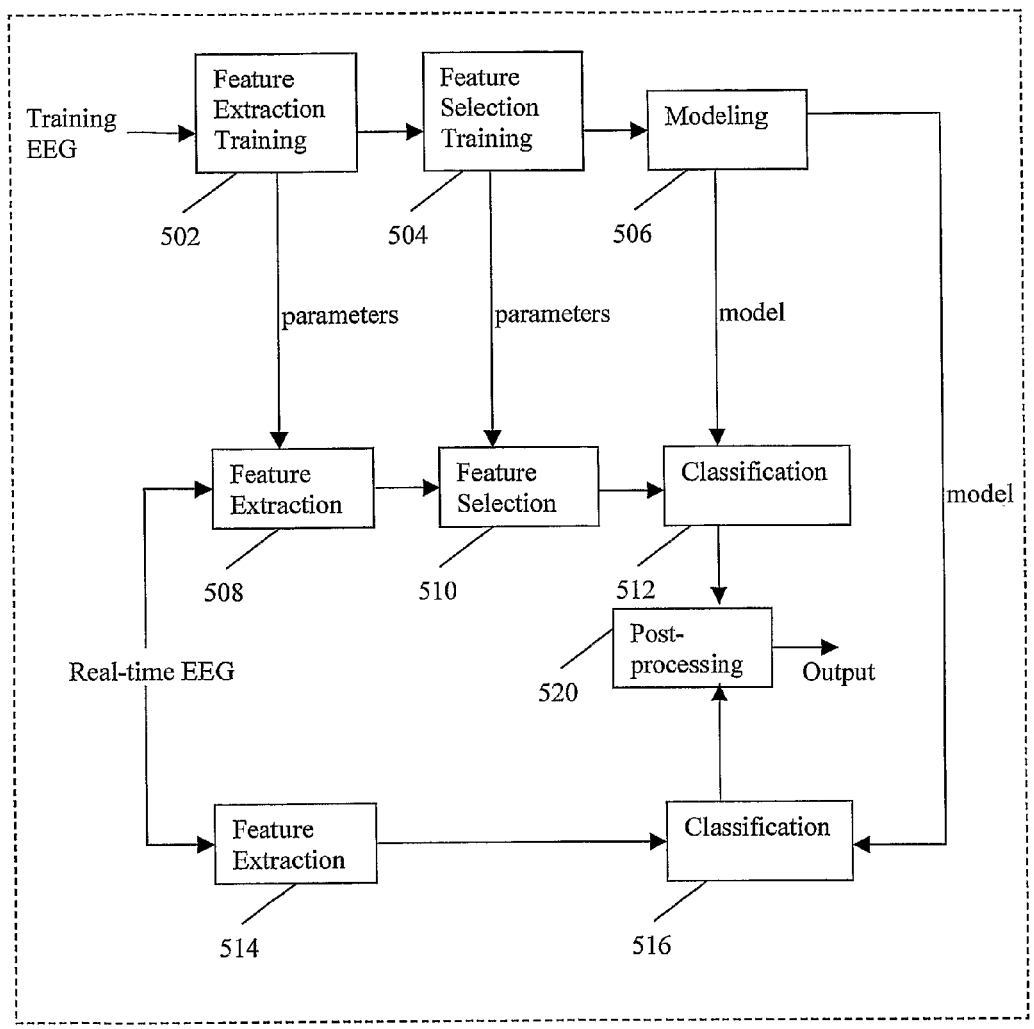
FIG. 5 shows a schematic block diagram illustrating the connection between a method for concentration detection and a subject-dependent training approach according to an embodiment of the present invention.
Figure 6:
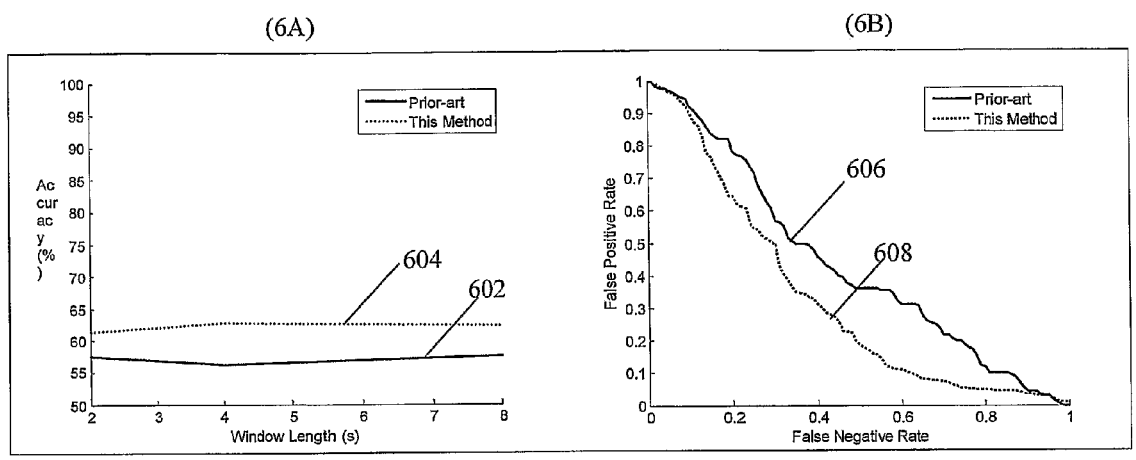
FIGS. 6a and b illustrate the results for subject 1 when a method for concentration detection according to an embodiment of the present invention and a prior art method are used.
Figure 7:
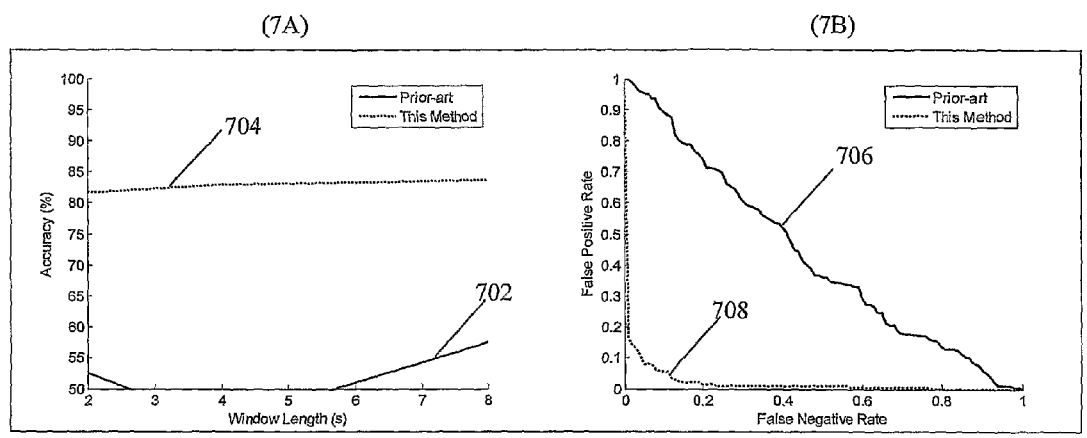
FIGS. 7a and b illustrate the results for subject 2 when a method for concentration detection according to an embodiment of the present invention and a prior art method are used.
Figure 8:
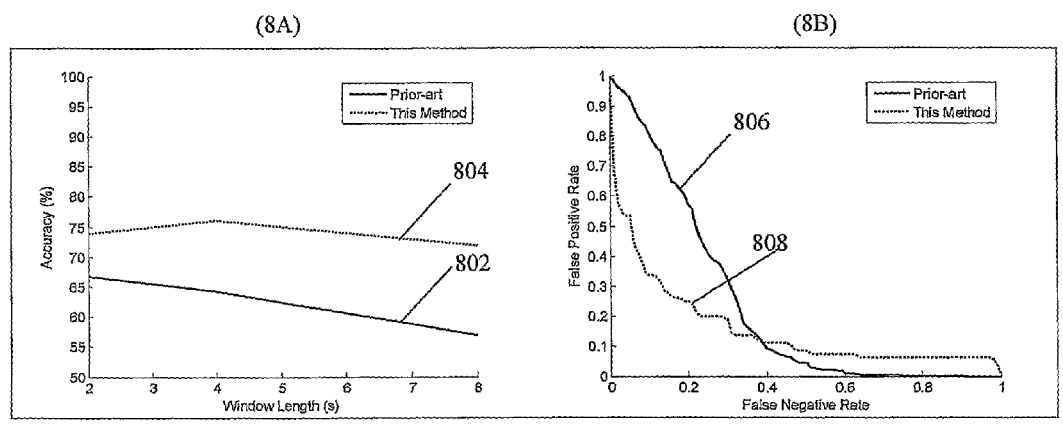
FIGS. 8a and b illustrate the results for subject 3 when a method for concentration detection according to an embodiment of the present invention and a prior art method are used.
Figure 9:
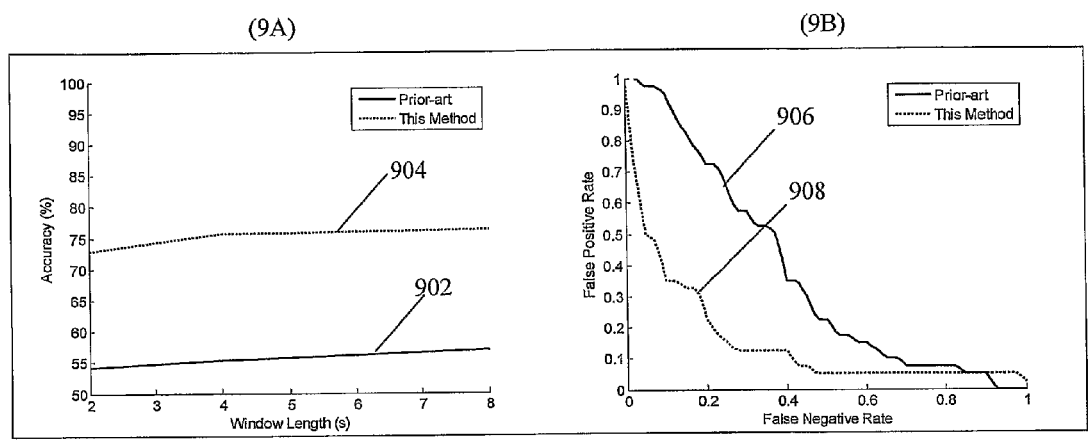
FIGS. 9a and b illustrate the results for subject 4 when a method for concentration detection according to an embodiment of the present invention and a prior art method are used.
Figure 10:
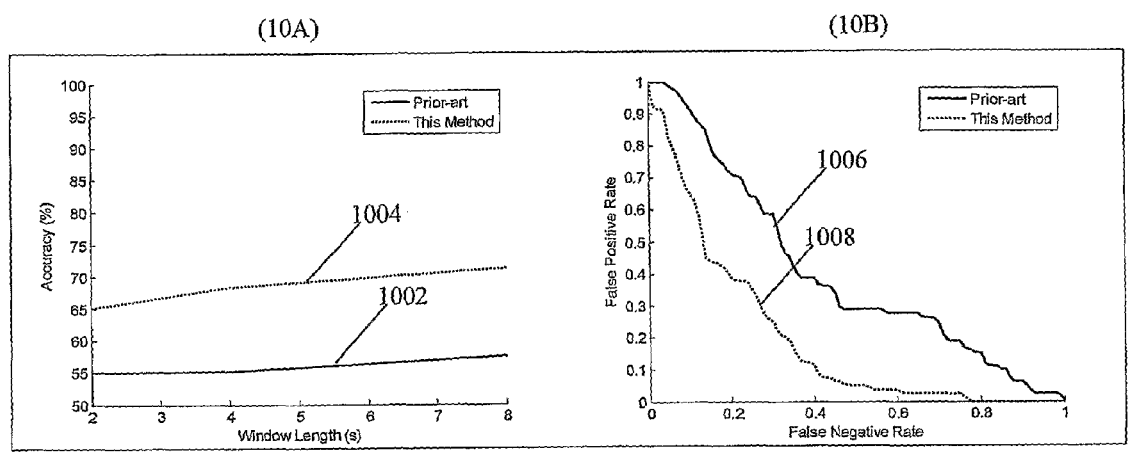
FIGS. 10a and b illustrate the results for subject 5 when a method for concentration detection according to an embodiment of the present invention and a prior art method are used.

FIG. 5 shows a schematic block diagram illustrating the connection between a method for concentration detection and a subject-dependent training approach according to an embodiment of the present invention. In one example, units 502, 504 and 506 correspond to the subject-dependent training approach, units 508, 510 and 512 correspond to the spectral-spatial feature extraction module in the method 300 in FIG. 3 and units 514 and 516 correspond to the temporal feature extraction module in the method 300 in FIG. 3.

In FIG. 5, training EEGs are acquired from the subjects when they are performing the required tasks during the training data collection sessions implemented in the subject-dependent training approach in the example embodiments. Machine learning techniques are then implemented in using the training EEGs in the feature extraction training unit 502, feature selection training unit 504 and the modelling unit 506 in FIG. 5. This would obtain the required parameters and model for the feature extraction unit 508, feature selection unit 510 and the classification units 512 and 516 for the online processing of real-time EEGs.

In FIG. 5, in one example, the feature extraction unit 508 implements steps 310 and 312 in FIG. 3 whereas the feature extraction unit 514 implements the step 306. In addition, the feature selection unit 510 implements the step 314. Furthermore, the classification units, 516 and 512, implement steps 308 and 316 in FIG. 3 respectively whereas the post-processing unit 520 implements steps 318 and 320 in FIG. 3.

The advantages conferred by the embodiments of the present invention can include:

Firstly, the method for concentration detection in the example embodiments provides an accurate quantitative measure of the subject's attention or concentration level that is not provided by any of the prior arts. The method in the example embodiments is subject-specific and uses optimized parameters. On the other hand, the prior art methods are based on spectral features alone, with their output typically based on the average of a large set of results and a comparison performed within a narrow range to detect concentration. For example, the range can be extending from the mean minus the standard deviation to the mean plus the standard deviation of the results. Hence, the method in the example embodiments is more accurate. Furthermore, in the example embodiments of the present invention, an accurate score can be obtained continuously and this is important in (near) real-time situations when a fast and accurate score is necessary.

Secondly, the hybrid model approach implemented in the example embodiments of the present invention takes all dimensions of the EEG into consideration. Specifically, these dimensions are the temporal, spatial and spectral information of the EEG which are then combined to give a single result. On the other hand, prior arts only concentrate on the spectral information of the EEG and hence provide a less detailed picture of the subject's EEG characteristics as compared to the embodiments of the present invention. In addition, in the example embodiments, the windowing approach allows the method of concentration detection to adjust the time resolution by changing the time segmentation window size to the best window size. This allows different window sizes to be chosen under different circumstances. For example, when a long term score is desired, the EEG recording session is preferably long whereas in a real-time situation, the EEG recording segment is preferably short.

Thirdly, the method in the example embodiments of the present invention allows the creation of the best model for each subject. The method can also be used to create models based on a small cohort and thus, investigate group-specific issues for example, a group of ADHD boys. Furthermore, using a large database, the method can also be useful in investigating generalization issues for example population based medical studies.

Fourthly, in the example embodiments, automatic selection and combination of features is achieved as the parameters and models for the method are automatically obtained from subject-specific modelling. This can improve the performance of the concentration detection method in the example embodiments. The mutual information feature selection in the example embodiments provides a novel way to create subject-specific modelling for example, for individualized healthcare, gaming, sport, etc. Furthermore, the use of the subject-specific model in the example embodiments achieves a higher accuracy and the machine learning methods used to create the subject-specific models allow the method in the example embodiments to be more flexible.

Fifthly, in the example embodiments, the metric used in the overall performance evaluation is based on receiver operating characteristics (ROC) analysis. In the example embodiments, performance curves plotting the False Positive Rate (FPR) against the False Negative Rate are used to analyze the ROC. This metric (ROC) shows objectively the true performance of the method in the example embodiments using a simple curve. It will also allow one to determine the best model to be used for each subject and also to choose a model that will fit the sensitivity and specificity requirements along the ROC curve, while taking note of the trade-off between the sensitivity and specificity.

In addition, unlike Cowan and Prell [Cowan and Prell, 1999—U.S. Pat. No. 5,983,129—Method for determining an individual's intensity of focused attention and integrating same into computer program], the embodiments of the present invention can provide a unified score for all subjects through a data-driven method. The method in the example embodiments also takes into consideration spectral, spatial and temporal changes and is hence more accurate than the method in Cowan and Prell. Furthermore, the method in the example embodiments is automatic unlike Cowan and Prell which requires manual adjustment of the parameters for different subjects.

Furthermore, the method in the example embodiments can be implemented in the form of a software tool for example, as add-ons to EEG systems or as internet-based web services. The method can also be embedded into a PDA-like medical device. Even with only a low-cost EEG acquired at a low sampling rate and from a few EEG sensors on the forehead, the method in the example embodiments is still able to provide robust attention or concentration detection and scoring. Thus, the method in the example embodiments can be implemented in a simple and handy system with only forehead sensors.

Hence, the example embodiments of the present invention can provide a continuous, quantitative, accurate and robust scoring mechanism for subject attention or concentration level since the example embodiments are based on features extracted and further selected using a multi-domain (spatial, spectral and temporal) analysis of the EEG and classified using machine learning. In addition, the example embodiments of the present invention provide a system to capture subject-specific EEG characteristics into a computational model and an automated parameter selection process that can find the best parameters and model. Furthermore, the example embodiments of the present invention provide a post-processing fusion scheme that improves performance by a multi-scale approach.

To further illustrate the advantages of the example embodiments of the present invention, an experimental study involving 5 participating subjects (all male and healthy) was carried out. The EEGs from these subjects are recorded from a standard 10/20 EEG system (NeuroScan NuAmps) with 15 channels and from frontal channels (Fp1/Fp2).

Table 1 shows the results achieved by a method for concentration detection according to an embodiment of the present invention and by the prior art method in Monastra and Lubar [Monastra and Lubar, 2000—U.S. Pat. No. 6,097, 980—Quantitative electroencephalographic (QEEG) process and apparatus for assessing attention deficit hyperactivity disorder; V. J. Monastra, S. Lynn, M. Linden, J. F. Lubar, J. Gruzelier, and T. J. LaVaque, "Electroencephalographic Biofeedback in the Treatment of Attention-Deficit/Hyperactivity Disorder," Applied Psychophysiology and Biofeedback, vol. 30, no. 2, pp. 95-114, June 2005.] In Table 1, the row corresponding to "Theta/beta (prior-art)" shows the mean accuracy obtained by the method according to the prior art, the row corresponding to "Waveform only" shows the mean accuracy obtained from the temporal feature extraction module alone the row corresponding to "Spectrum only" shows the mean accuracy obtained from the spectral-spatial feature extraction module alone and the row corresponding to "Hybrid technique" shows the mean accuracy obtained from the method in the example embodiments. Furthermore, the results in Table 1 are in percentage, expressed in the form "mean±standard deviation" and are obtained via a 2×2 fold cross-validation method. From Table 1, it can be seen that the mean accuracy of the method in the example embodiments is significantly better than that of the prior art method. More specifically, the overall performance improvement (absolute value) of the method in the example embodiments over the prior art method is 14.8%. Thus, these results demonstrate the ability of the method in the example embodiments to create an optimized subject-specific model that outperforms the prior art method.

TABLE 1

|  | Subject 1 | Subject 2 | Subject 3 | Subject 4 | Subject 5 | Average |
|---|---|---|---|---|---|---|
| Theta/beta (prior-art) | 57.5 ± 2.7 | 57.5 ± 3.5 | 66.7 ± 10.9 | 56.9 ± 9.7 | 57.5 ± 2.2 | 59.2 |
| Waveform only | 60.2 ± 3.8 | 78.8 ± 5.3 | 69.8 ± 4.7 | 76.3 ± 5.3 | 72.8 ± 6.2 | 71.6 |
| Spectrum only | 64.4 ± 4.0 | 87.9 ± 6.2 | 72.8 ± 3.2 | 76.3 ± 0.0 | 59.6 ± 8.9 | 72.2 |
| Hybrid technique | 62.8 ± 4.4 | 83.8 ± 3.5 | 76.0 ± 1.0 | 76.3 ± 1.7 | 71.3 ± 5.3 | 74.0 |
| Improvement | 5.3 | 26.3 | 9.3 | 19.4 | 13.8 | 14.8 |

Table 2 shows further results achieved by a method for concentration detection according to an embodiment of the present invention and by the prior art method in Monastra and Lubar. In Table 2, for each subject, the row corresponding to "Theta/beta (prior-art)" shows the equal error rate (EER) obtained by the method according to the prior art, the row corresponding to "Waveform only" shows the EER obtained from the temporal feature extraction module alone, the row corresponding to "Spectrum only" shows the EER obtained from the spectral-spatial feature extraction module alone and the row corresponding to "Hybrid technique" shows the EER obtained from the method in the example embodiments. The EER is the rate at which the false positive rate and the false negative rate are equal. Furthermore, the results in Table 2 are in percentage, expressed in the form "mean±standard deviation" and are obtained via a 2×2 fold cross-validation method. For each subject, the best performance by each of the methods is tabulated in Table 2. The relative error reduction rate is calculated according to Equation (18). It can be seen from Table 2 that the overall error rate reduction is 42.5% indicating that the method in the example embodiments performs significantly better than the prior art method. Furthermore, Table 2 also shows that even the performance of the temporal feature extraction module alone ("Waveform only") or the spectral-spatial feature extraction module alone ("Spectral only") in the example embodiments is better than the prior art method. This illustrates that the subject dependent training approach can significantly improve the performance of the methods.

TABLE 2

|  | Subject 1 | Subject 2 | Subject 3 | Subject 4 | Subject 5 | Average |
|---|---|---|---|---|---|---|
| Theta/beta (prior-art) | 42.7 | 44.1 | 30.6 | 39.3 | 38.7 | 39.1 |
| Waveform only | 39.2 | 17.9 | 27.5 | 17.8 | 33.9 | 27.3 |
| Spectrum only | 37.9 | 8.2 | 21.9 | 25.1 | 30.6 | 24.7 |
| Hybrid technique | 35.0 | 7.3 | 21.9 | 20.8 | 27.7 | 22.5 |
| Improvement (Relative Error Reduction Rate) | 18 | 83.4 | 28.4 | 47.0 | 29.7 | 42.5 |

$$\text{Relative Error Reduction Rate} = \frac{EER_{prior\ art} - EER_{hybrid}}{EER_{prior\ art}} \quad (18)$$

FIGS. 6-10 illustrate the results for subjects 1-5 respectively when a method for concentration detection according to an embodiment of the present invention and the prior art method in Monastra and Lubar are used. In FIGS. 6-10, the accuracy in percentage under various window-length conditions is shown in FIGS. 6A, 7A, 8A, 9A and 10A respectively whereby curves 602, 702, 802, 902 and 1002 represent the accuracy obtained with the prior art method and curves 604, 704, 804, 904 and 1004 represent the accuracy obtained with the method in the embodiments of the present invention. Furthermore, the performance curves with base window-length condition are shown in FIGS. 6B, 7B, 8B, 9B and 10B respectively whereby curves 606, 706, 806, 906 and 1006 represent the performance curves obtained with the prior art method and curves 608, 708, 808, 908 and 1008 represent the performance curves obtained with the method in the embodiments of the present invention. The performance curves in FIGS. 6-10 are obtained using the window sizes as specified below. For subjects 1 and 3, the window size is 2 seconds for the prior art method and 4 seconds for the method in the example embodiments. For subject 2, the window size is 8 seconds for the prior art method and 2 seconds for the method in the example embodiments. For subject 4, the window size is 4 seconds for the prior art method and 8 seconds for the method in the example embodiments. For subject 5, the window size is 8 seconds for the prior art method and 8 seconds for the method in the example embodiments.

Figure 11:
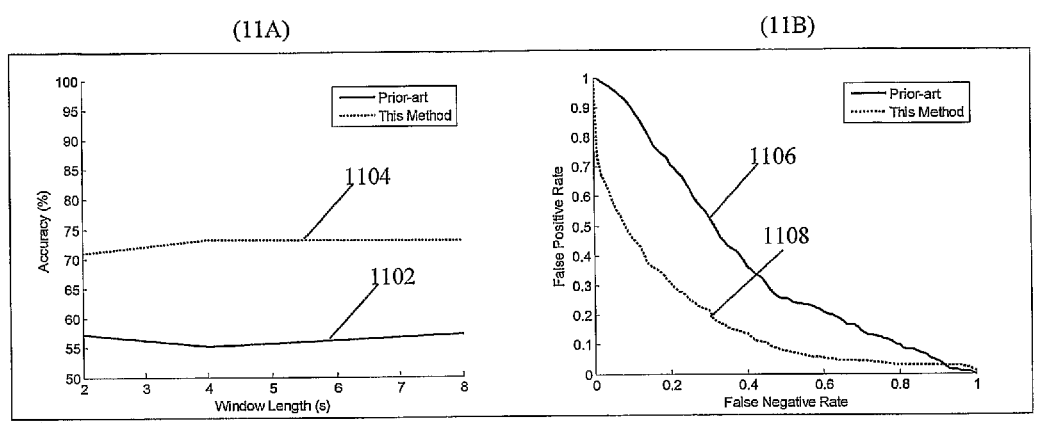
FIGS. 11a and b illustrate the average results for subjects 1-5 when a method for concentration detection according to an embodiment of the present invention and a prior art method are used.

FIG. 11 illustrates the average results across subjects 1-5 when a method for concentration detection according to an embodiment of the present invention and the prior art method in Monastra and Lubar are used. In FIG. 11, FIG. 11A illustrates the average accuracy across the 5 subjects whereas FIG. 11B illustrates the average performance curve across the 5 subjects. In FIG. 11A, curve 1102 represents the average accuracy obtained with the prior art method and curve 1104 represents the average accuracy obtained with the method in the embodiments of the present invention. In addition, in FIG. 11B, curve 1106 represents the average performance curve obtained with the prior art method and curve 1108 represents the average performance curve obtained with the method in the embodiments of the present invention.

From FIGS. 6-11, it can be seen that the method in the embodiments of the present invention can achieve a higher accuracy and an improved performance curve as compared to the prior art method.

Figure 12:
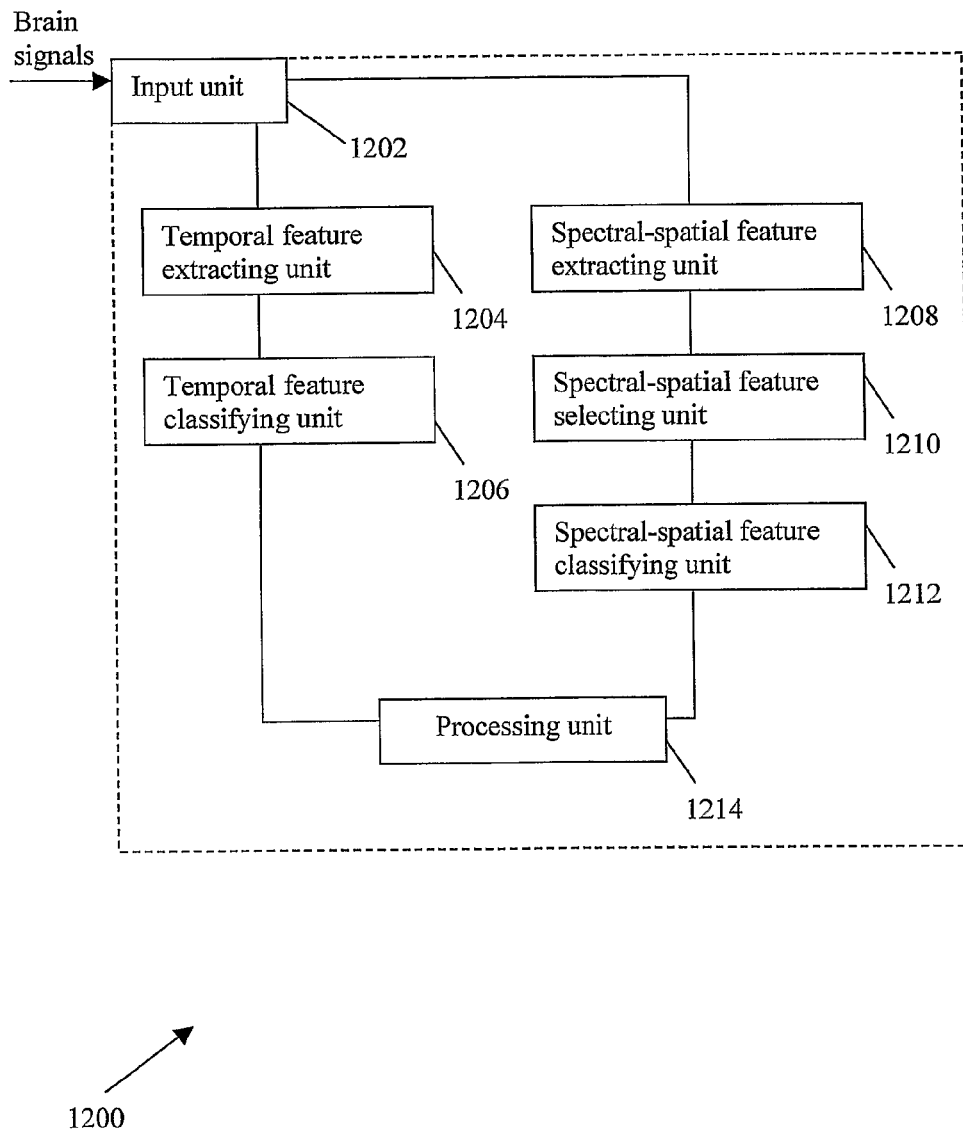
FIG. 12 illustrates a schematic block diagram of a system for concentration detection according to an embodiment of the present invention.

FIG. 12 illustrates a schematic block diagram of a system 1200 for concentration detection according to an embodiment of the present invention. The system 1200 includes an input unit 1202 for receiving brain signals, a temporal feature extracting unit 1204 for extracting temporal features from brain signals, a temporal feature classifying unit 1206 for classifying the extracted temporal features using a classifier to give a score $x_1$, a spectral-spatial feature extracting unit 1208 for extracting spectral-spatial features from brain signals, a spectral-spatial feature selecting unit 1210 for selecting spectral-spatial features containing discriminative information between the concentration and non-concentration states from the set of extracted spectral-spatial features, a spectral-spatial feature classifying unit 1212 for classifying the selected spectral-spatial features using a classifier to give a score $x_2$ and a processing unit 1214 coupled to the temporal feature classifying unit 1206 and the spectral-spatial feature classifying unit 1212 for combining the scores $x_1$ and $x_2$ to give a single score and for determining if the subject is in a concentration state based on the single score.

Figure 13:
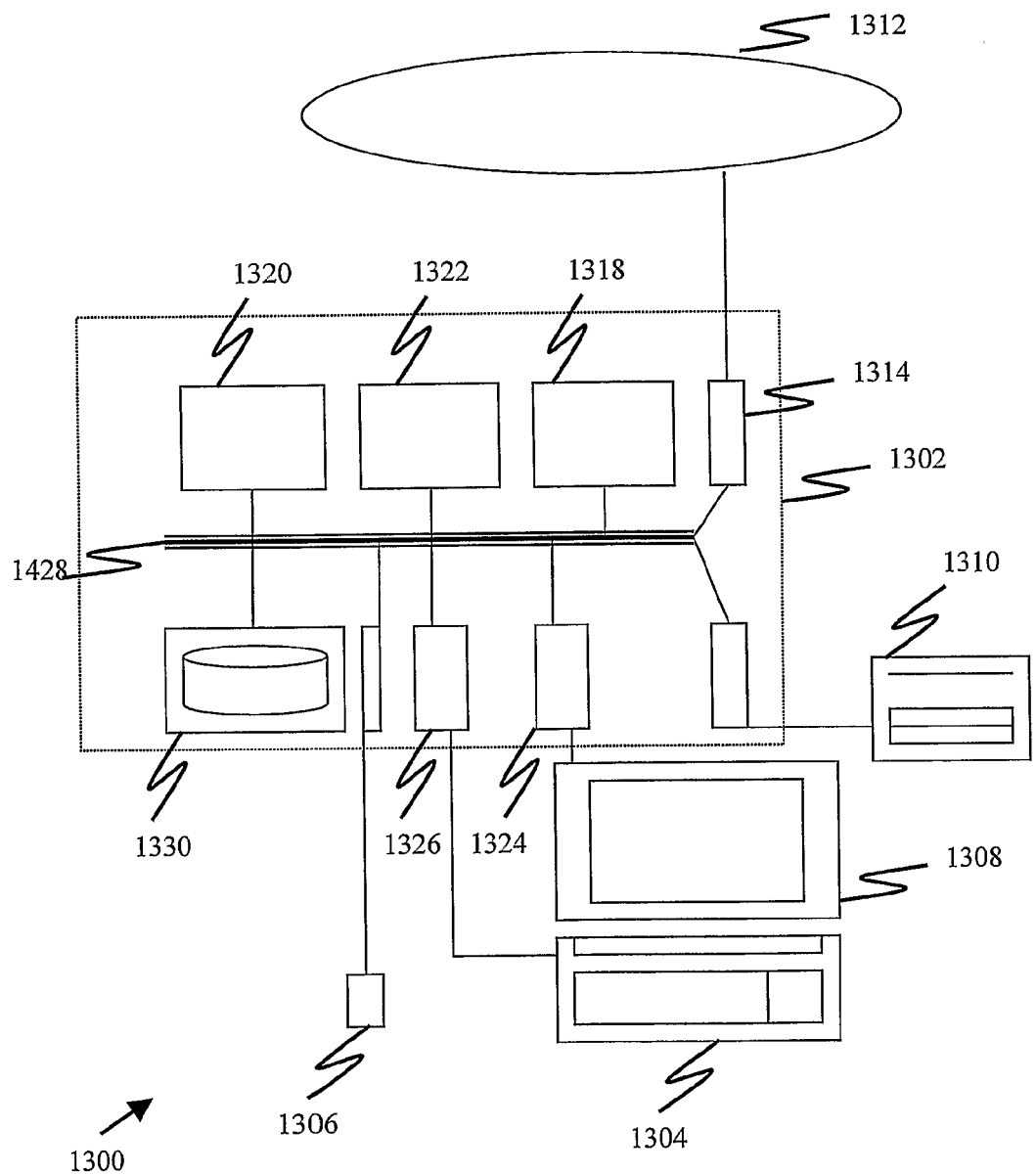
FIG. 13 illustrates a schematic block diagram of a computer system on which the method and system of the example embodiments can be implemented.

The method and system of the example embodiments can be implemented on a computer system 1300, schematically shown in FIG. 13. The method may be implemented as software, such as a computer program being executed within the computer system 1300, and instructing the computer system 1300 to conduct the method of the example embodiment.

The computer system 1300 comprises a computer module 1302, input modules such as a keyboard 1304 and mouse 1306 and a plurality of output devices such as a display 1308, and printer 1310.

The computer module 1302 is connected to a computer network 1312 via a suitable transceiver device 1314, to enable access to e.g. the Internet or other network systems such as Local Area Network (LAN) or Wide Area Network (WAN).

The computer module 1302 in the example includes a processor 1318, a Random Access Memory (RAM) 1320 and a Read Only Memory (ROM) 1322. The computer module 1302 also includes a number of Input/Output (I/O) interfaces, for example I/O interface 1324 to the display 1308, and I/O interface 1326 to the keyboard 1304.

The components of the computer module 1302 typically communicate via an interconnected bus 1328 and in a manner known to the person skilled in the relevant art.

The application program is typically supplied to the user of the computer system 1300 encoded on a data storage medium such as a CD-ROM or flash memory carrier and read utilising a corresponding data storage medium drive of a data storage device 1330. The application program is read and controlled in its execution by the processor 1318. Intermediate storage of program data may be accomplished using RAM 1320.

Figure 14:
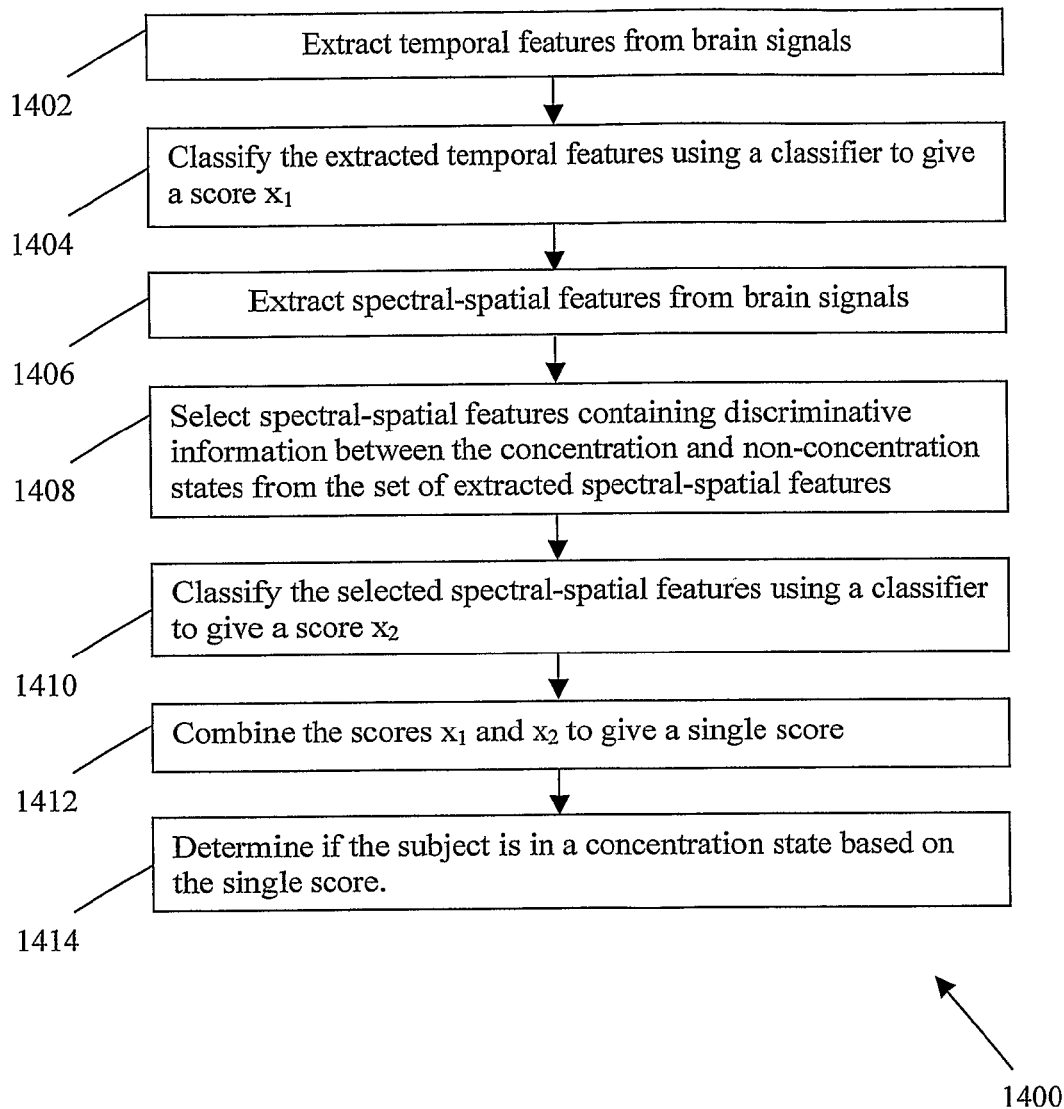
FIG. 14 shows a flowchart illustrating a method for concentration detection according to an embodiment of the present invention.

FIG. 14 shows a flowchart illustrating a method 1400 for concentration detection according to an embodiment of the present invention. At step 1402, temporal features from brain signals are extracted. At step 1404, the extracted temporal features are classified using a classifier to give a score $x_1$. At step 1406, spectral-spatial features from brain signals are extracted and at step 1408, spectral-spatial features containing discriminative information between the concentration and non-concentration states are selected from the set of extracted spectral-spatial features. At step 1410, the selected spectral-spatial features are classified using a classifier to give a score $x_2$. At step 1412, the scores $x_1$ and $x_2$ are combined to give a single score and at step 1414, it is determined if the subject is in a concentration state based on the single score.

Figure 15:
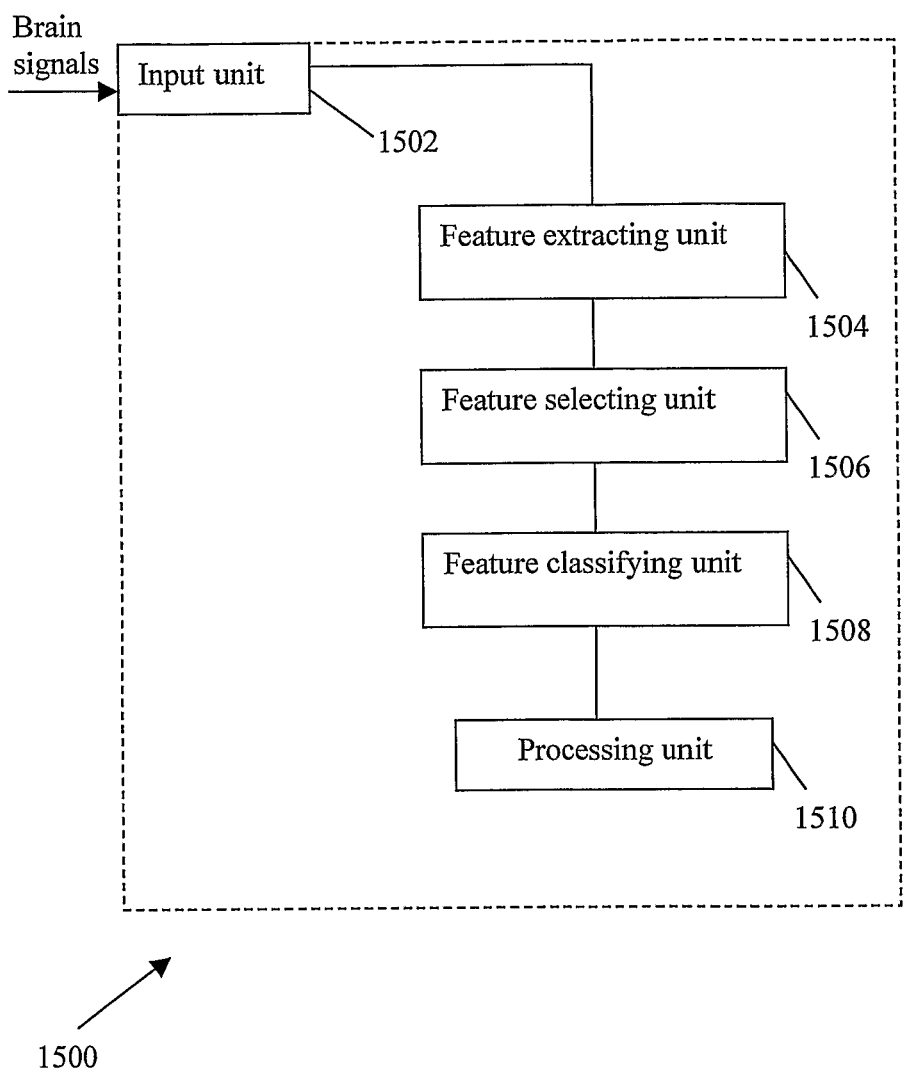
FIG. 15 illustrates a schematic block diagram of a system for concentration detection according to an embodiment of the present invention.

FIG. 15 illustrates a schematic block diagram of a system 1500 for concentration detection according to an embodiment of the present invention. The system 1500 includes an input unit 1502 for receiving brain signals, a feature extracting unit 1504 for extracting features from brain signals, a feature selecting unit 1506 for selecting features containing discriminative information between concentration and non-concentration states from the set of extracted features, a feature classifying unit 1508 for classifying the selected features using a classifier to give a score and a processing unit 1510 for determining if the subject is in a concentration state based on the score. In the system 1500, subject dependant training data is used to generate parameters for extracting the features from the brain signals, for selecting the features containing discriminative information between the concentration and non-concentration states from the set of extracted features and for classifying the selected features using a classifier.

Figure 16:
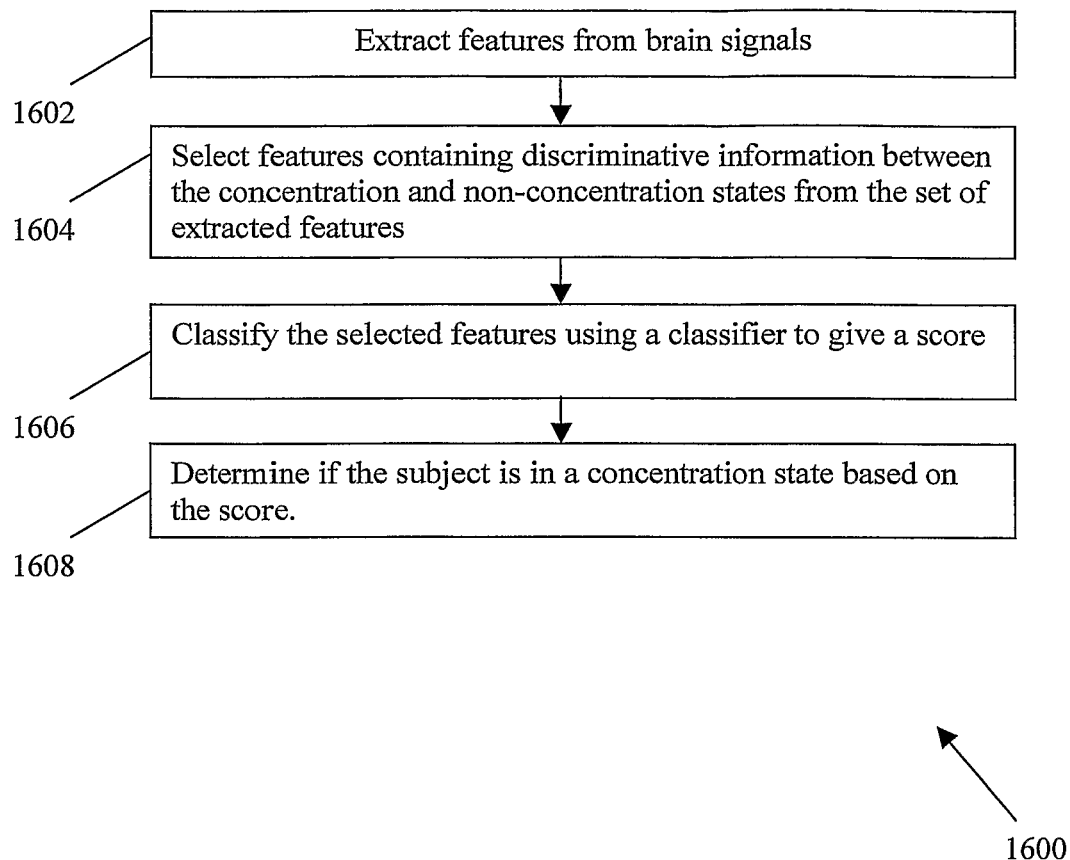
FIG. 16 shows a flowchart illustrating a method for concentration detection according to an embodiment of the present invention.

FIG. 16 shows a flowchart illustrating a method 1600 for concentration detection according to an embodiment of the present invention. At step 1602, features are extracted from brain signals. At step 1604, features containing discriminative information between concentration and non-concentration states are selected from the set of extracted features. At step 1606, selected features are classified using a classifier to give a score. In step 1608, it is determined if the subject is in a concentration state based on the score. In method 1600, subject dependant training data is used to generate parameters for extracting the features from the brain signals, for selecting the features containing discriminative information between the concentration and non-concentration states from the set of extracted features and for classifying the selected features using a classifier.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive. For example, while the use of EEG has been described in the example embodiments of the present invention, other types of brain signals such as MEG signals or a mixture of both MEG and EEG signals can also be used.

The invention claimed is:

1. A method for concentration detection, the method comprising the steps of:

extracting temporal features from brain signals;
classifying the extracted temporal features using a classifier to give a score $x_1$;
extracting spectral-spatial features from brain signals;
selecting spectral-spatial features containing discriminative information between concentration and non-concentration states from the set of extracted spectral-spatial features;
classifying the selected spectral-spatial features using a classifier to give a score $x_2$;
combining the scores $x_1$ and $x_2$ to give a single score; and
determining whether the subject is in a concentration state based on the single score;
wherein the step of extracting spectral-spatial features of brain signals further comprises the steps of:
extracting respective brain signal components in discrete frequency windows using filter banks to obtain spectral features of brain signals; and
applying a common spatial pattern (CSP) algorithm to each of the spectral features using a CSP array to obtain the spectral-spatial features of brain signals.

2. The method as claimed in claim 1, wherein the step of extracting temporal features from brain signals further comprises the steps of:

computing statistics of brain waveforms in each of a plurality of electrode channels; and
concatenating the statistics into a joint feature vector.

3. The method as claimed in claim 2, wherein the statistics of the brain waveforms are standard deviations.

4. The method as claimed in claim 1, wherein said filter banks comprise low-order bandpass Chebyshev Type II filters with a pass-band width of 4 Hertz (Hz).

5. The method as claimed in claim 1, wherein the step of selecting spectral-spatial features containing discriminative information between concentration and non-concentration states from the set of extracted spectral-spatial features further comprises the step of selecting spectral-spatial features based on the mutual dependence of the features with respect to the concentration and non-concentration states.

6. The method as claimed in claim 1, wherein the step of combining the scores $x_1$ and $x_2$ to give a single score further comprises the steps of:
normalizing the scores $x_1$ and $x_2$ according to an equation $(x-m_x)/s_x$ whereby $m_x$ and $s_x$ are the mean and standard deviation of outputs from the classifiers using training samples to give $x_{1n}$ and $x_{2n}$ respectively;
assigning weights $w_1$ and $w_2$ to normalized scores $x_{1n}$ and $x_{2n}$ respectively; and
combining the scores $x_{1n}$ and $x_{2n}$ according to an equation $x_{1n}*w_1 + X_{2n}*w_2$ to give a single score.

7. The method as claimed in claim 6 wherein said weights $w_1$ and $w_2$ are calculated according to the equation $w_i=(y_i)^p$ where $y_i$ is the classification accuracy in classifying the extracted temporal features when i=1 and in classifying the extracted spectral-spatial features when i=2 and p (p>0) controls the power of $w_i$ in the calculation of the single score.

8. The method as claimed in claim 1, wherein the step of determining whether the subject is in a concentration state based on the single score further comprises determining that the subject is in a concentration state when the single score is higher than a threshold and that the subject is not in a concentration state when the single score is lower than a threshold.

9. The method as claimed in claim 1, wherein said classifier comprises one or more of a group consisting of a Linear Discriminant Analysis classifier, Neural Networks, Support Vector Machines, Fuzzy Inference System, Tree-based classifiers, Fuzzy Type 2 and Relevance Vector Machine.

10. The method as claimed in claim 1, the method further comprises the step of using training data to generate parameters for classifying the extracted temporal features using a classifier, for extracting spectral-spatial features from brain signals, for selecting spectral-spatial features containing discriminative information between the concentration and non-concentration states from the set of extracted spectral-spatial features and for classifying the selected spectral-spatial features using a classifier.

11. The method as claimed in claim 10, wherein said parameters comprise one or more of a group consisting of projection matrices of CSPs for the CSP algorithm, parameters for selecting spectral-spatial features based on mutual information and a model for the classifiers.

12. The method as claimed in claim 10, wherein said step of using training data to generate parameters further comprises the steps of:
collecting training data from subjects performing a set of tasks; and
determining said parameters via machine learning methods.

13. The method as claimed in claim 12, wherein said set of tasks comprises one or more of a group consisting of reading a technical paper, performing mental arithmetic with closed eyes, relaxing and looking around, and resting with closed eyes.

14. A system for concentration detection, the system comprising:
an input device for receiving brain signals;
a temporal feature extracting unit for extracting temporal features from the brain signals;
a temporal feature classifying unit for classifying the extracted temporal features using a classifier to give a score $x_1$;
a spectral-spatial feature extracting unit for extracting spectral-spatial features from the brain signals;
a spectral-spatial feature selecting unit for selecting spectral-spatial features containing discriminative information between the concentration and non-concentration states from the set of extracted spectral-spatial features;
a spectral-spatial feature classifying unit for classifying the selected spectral-spatial features using a classifier to give a score $x_2$; and
a processing unit, including a memory, coupled to said temporal feature classifying unit and said spectral-spatial feature classifying unit for combining the scores $x_1$ and $x_2$ to give a single score and for determining whether the subject is in a concentration state based on the single score;
wherein the spectral-spatial feature extracting unit comprises:
filter banks to extract respective brain signal components in discrete frequency windows to obtain spectral features of the brain signals; and
a common spatial pattern (CSP) array to apply a CSP algorithm to each of the spectral features to obtain the spectral-spatial features of the brain signals.

15. The system as claimed in claim 14, wherein said filter banks comprise low-order bandpass Chebyshev Type II filters with a pass-band width of 4 Hertz (Hz).

16. A non-transitory computer-readable medium having stored thereon computer code means comprising executable instruction for instructing a computer system to execute a method for concentration detection, the method comprising the steps of:
extracting temporal features from brain signals;
classifying the extracted temporal features using a classifier to give a score $x_1$;
extracting spectral-spatial features from brain signals;
selecting spectral-spatial features containing discriminative information between the concentration and non-concentration states from the set of extracted spectral-spatial features;
classifying the selected spectral-spatial features using a classifier to give a score $x_2$;
combining the scores $x_1$ and $x_2$ to give a single score; and
determining whether the subject is in a concentration state based on the single score;
wherein the step of extracting spectral-spatial features of brain signals further comprises the steps of:
extracting respective brain signal components in discrete frequency windows using filter banks to obtain spectral features of brain signals; and
applying a common spatial pattern (CSP) algorithm to each of the spectral features using a CSP array to obtain the spectral-spatial features of brain signals.

17. A method for concentration detection, the method comprising the steps of:
extracting features from brain signals;
selecting features containing discriminative information between concentration and non-concentration states from the set of extracted features;

classifying the selected features using a classifier to give a score;

wherein subject dependant training data is used to generate parameters for a Common Spatial Pattern (CSP) algorithm for extracting the features from the brain signals, for selecting the features containing discriminative information between the concentration and non-concentration states from the set of extracted features and for classifying the selected features using a classifier; and determining whether the subject is in a concentration state based on the score, wherein the step of determining whether the subject is in a concentration state based on the score comprises determining that the subject is in a concentration state when the score is higher than a threshold and that the subject is not in a concentration state when the score is lower than a threshold.

18. A system for concentration detection, the system comprising:

an input device for receiving brain signals;

a feature extracting unit for extracting features from the brain signals;

a feature selecting unit for selecting features containing discriminative information between concentration and non-concentration states from the set of extracted features;

a feature classifying unit for classifying the selected features using a classifier to give a score;

wherein subject dependant training data is used to generate parameters for a common spatial pattern (CSP) algorithm for extracting the features from the brain signals, for selecting the features containing discriminative information between the concentration and non-concentration states from the set of extracted features and for classifying the selected features using a classifier; and a processing unit, including a memory, for determining whether the subject is in a concentration state based on the score, wherein determining whether the subject is in a concentration state based on the score comprises determining that the subject is in a concentration state when the score is higher than a threshold and that the subject is not in a concentration state when the score is lower than a threshold.

19. A non-transitory computer-readable medium having stored thereon computer code means comprising executable instructions for instructing a computer system to execute a method for concentration detection, the method comprising the steps of:

extracting features from brain signals;

selecting features containing discriminative information between concentration and non-concentration states from the set of extracted features;

classifying the selected features using a classifier to give a score;

wherein subject dependant training data is used to generate parameters for a common spatial pattern (CSP) algorithm for extracting the features from the brain signals, for selecting the features containing discriminative information between the concentration and non-concentration states from the set of extracted features and for classifying the selected features using a classifier; and determining whether the subject is in a concentration state based on the score, wherein the step of determining whether the subject is in a concentration state based on the score comprises determining that the subject is in a concentration state when the score is higher than a threshold and that the subject is not in a concentration state when the score is lower than a threshold.

* * * * *